(12) United States Patent
Stockert

(10) Patent No.: US 9,700,367 B2
(45) Date of Patent: Jul. 11, 2017

(54) DEVICE FOR THERMOSURGERY

(76) Inventor: Rüdiger Stockert, Freiburg (DE)

( * ) Notice: Subject to any disclaimer, the term of this patent is extended or adjusted under 35 U.S.C. 154(b) by 1759 days.

(21) Appl. No.: 12/920,510

(22) PCT Filed: Mar. 3, 2008

(86) PCT No.: PCT/EP2008/001677
§ 371 (c)(1),
(2), (4) Date: Oct. 26, 2010

(87) PCT Pub. No.: WO2009/109197
PCT Pub. Date: Sep. 11, 2009

(65) Prior Publication Data
US 2011/0208183 A1    Aug. 25, 2011

(51) Int. Cl.
*A61B 18/16*  (2006.01)
*A61B 18/12*  (2006.01)
*A61B 18/14*  (2006.01)
*A61B 18/00*  (2006.01)

(52) U.S. Cl.
CPC ...... *A61B 18/1233* (2013.01); *A61B 18/1206* (2013.01); *A61B 18/16* (2013.01); *A61B 18/1477* (2013.01); *A61B 2018/00678* (2013.01); *A61B 2018/00875* (2013.01); *A61B 2018/1425* (2013.01)

(58) Field of Classification Search
CPC ............ A61B 18/1206; A61B 18/1233; A61B 18/1477; A61B 18/16; A61B 2018/00666; A61B 2018/00678; A61B 2018/00875; A61B 2018/1425

USPC ........................................ 606/34, 35, 37, 38
See application file for complete search history.

(56) References Cited

U.S. PATENT DOCUMENTS

2004/0059323 A1    3/2004   Strum et al.

FOREIGN PATENT DOCUMENTS

EP           1808144 A2    7/2007
WO        2005110263 A2   11/2005
WO     WO/2009/109197     9/2009

*Primary Examiner* — Michael Peffley
*Assistant Examiner* — Samantha Good
(74) *Attorney, Agent, or Firm* — Robert R. Deleault, Esq.; Mesmer & Deleault, PLLC

(57) ABSTRACT

The invention relates to a device (10) for thermosurgery. The device (10) comprises a generator (12) for supplying high frequency electrical treatment energy, an interface connection arrangement (14) which permits the connection of a plurality of electrodes to be placed on or in the body of a patient (18), the electrodes comprising an application electrode (16) to be positioned in the area of the treatment site and a plurality of planar counter-electrodes (21, 22, 26, 27), and impedance measurement means (30, 35, 40) which permit impedance measurement in a plurality of measurement circuits, each of which passes via at least one counter-electrode (21, 22, 26, 27) connected to the interface connection arrangement (14).

10 Claims, 6 Drawing Sheets

DEVICE FOR THERMOSURGERY

BACKGROUND OF THE INVENTION

The invention relates to a device for thermosurgery.

In thermosurgery, biological tissue is heated by the introduction of treatment energy in order to achieve a specific therapeutic goal by denaturing the treated tissue. In particular, it is intended in thermosurgery to achieve coagulation or ablation of local tissue zones, for example on the interior wall of the cardiac ventricles, on the cardiac valves, on cardiac veins and arteries or other blood vessels of the human or animal body. Thermosurgery may be used on the heart for example to treat cases of arrhythmic or tachycardia. It will be understood that the field of application of the thermosurgical device according to the invention is not restricted to cardiac treatment. In principle, the device according to the invention is suitable for the thermosurgical treatment of any desired areas on or within the body.

Monopolar and bipolar applications are known in electrical HF thermosurgery. In both types of treatment, the high frequency alternating current used for treatment is introduced into the body via an application electrode, which is placed in the immediate vicinity of the tissue area to be treated. In the bipolar method, the circuit is completed by one or more planar counter-electrodes which are laid externally on the skin of the body remotely from the application electrode. The effective electrode area of the counter-electrodes is large in comparison with that of the application electrode, for which reason the current density at the counter-electrodes is low and there is no need to fear skin charring there under normal circumstances (i.e. good contact of the counter-electrodes with the skin).

The situation changes if the counter-electrodes become partially detached from the skin. In this case, the current density rises sharply in the areas of the counter-electrodes still in contact with the skin, so correspondingly increasing the risk of skin charring. Thermosurgical treatments may very easily last for several hours. Patient movement and sweating may impair the quality of the contact between the counter-electrodes and the skin. Experience has shown that, as treatment time increases, so too does the risk that the electrical contact between the counter-electrodes and the skin becomes poorer.

SUMMARY OF THE INVENTION

The object of the invention is to provide a device for thermosurgery which is reliably capable of avoiding unwanted tissue or skin burns.

To achieve this object, the invention provides a device for thermosurgery with a generator for supplying high frequency electrical treatment energy, an interface connection arrangement which permits the connection of a plurality of electrodes to be placed on or in the patient's body, the electrodes comprising an application electrode to be positioned in the area of the treatment site and a plurality of planar counter-electrodes, and impedance measurement means which permit impedance measurement in a plurality of measurement circuits where the plurality of measurement circuits include first, second and third measurement circuits, each of which passes via at least one counter-electrode connected to the interface connection arrangement.

The device according to the invention permits the determination of a plurality of impedance values of variable predictiveness, the tissue impedance from in each case a different part of the patient's body being an input variable in each impedance value. The combined predictiveness of the plurality of measured impedance values can then enable reliable identification of the counter-electrode on which there are contact problems, for example due to partial detachment of the electrode.

There are many and varied conceivable configurations of measurement circuits with which overall a plurality of different impedances may be measured. According to a further development of the invention, the interface connection arrangement may accordingly permit the connection of a plurality of counter-electrode units each with two counter-electrodes, the measurement circuits assigned to each counter-electrode unit each comprising a first measurement circuit in which the counter-electrodes of the counter-electrode unit in question are arranged electrically in series.

Alternatively or additionally, the interface connection arrangement may permit the connection of at least one counter-electrode unit with two counter-electrodes, the measurement circuits assigned to each of the counter-electrodes of the counter-electrode unit each comprising a second measurement circuit, in which is located only the counter-electrode in question of the counter-electrode unit, but not the in each case other counter-electrode of the counter-electrode unit. In this variant, the measurement circuits may furthermore comprise a first measurement circuit in which the counter-electrodes of the counter-electrode unit are arranged electrically in series. At least one, in particular each, of the second measurement circuits preferably also passes via the application electrode.

If the interface connection arrangement permits the connection of at least one needle electrode separate from the application electrode, at least one, in particular each, of the second measurement circuits may also pass via the needle electrode, but not via the application electrode. The needle electrode is an electrode which is capable of penetrating skin tissue and is generally placed beneath the skin. Instead of a needle electrode, it is also possible to use an adhesive electrode to be applied onto the outside of the skin.

The measurement circuits may furthermore comprise at least one third measurement circuit with two counter-electrode units arranged electrically in series, in which the counter-electrodes of each counter-electrode unit are arranged electrically parallel to one another. They may alternatively or additionally comprise a fourth measurement circuit passing via the application electrode and two or more, in particular all, of the counter-electrodes, in which circuit the counter-electrodes are arranged electrically parallel to one another.

The impedance measurement means may be configured to generate electrical auxiliary signals of in each case various frequencies differing from the frequency of the treatment energy and to supply each of the auxiliary signals to each at least one measurement circuit for impedance measurement in said measurement circuit. Filter means may here be provided which block at least a proportion of the auxiliary signal frequencies, but allow the frequency of the treatment energy and optionally at least one other auxiliary signal frequency to pass through. Such filter means may in particular be located in circuit branches via which the treatment current output by the generator flows. They may serve to ensure that specific auxiliary signals only flow in specific parts of the circuit so as not to distort the impedance measurement.

As an alternative or in addition to measurement of the impedances in various measurement circuits by frequency-division multiplexing, time-division multiplexing may be used, in which impedance measurement is carried out in various measurement circuits at different time slots.

The device may contain an evaluation and control arrangement which is configured to monitor at least one impedance measured variable representative of the impedance in one of the measurement circuits and/or at least one variable derived from the impedance measured variables of one or more measurement circuits and to bring about a predetermined response depending on whether at least one impedance measured variable and/or at least one derived variable fulfils a predetermined condition.

The evaluation and control arrangement may here bring about the predetermined response in particular depending on whether an impedance measured variable and/or a derived variable reaches a threshold value set as a function of at least one previous value of the impedance measured variable or of the derived variable. Such dynamic setting of threshold values is capable of taking account of the peculiarities of the particular patient and of the apparatus used in each case.

According to a further development of the present invention, the evaluation and control arrangement may be configured to set the threshold value as a function of a measured extreme value of the impedance measured variable or of the derived variable. The extreme value may, for example, be the minimum impedance value measured in one of the measurement circuits during a treatment. The threshold value may then be set, for example, by increasing the measured minimum by an absolute or percentage amount.

The evaluation and control arrangement may furthermore be configured to determine the ratio of the impedance measured variables of two different measurement circuits as a derived variable. Such ratio variables may be helpful in identifying the specific counter-electrode in which contact is becoming poorer and so is threatening to cause skin burns. This may in particular be achieved by in each case relating the impedance measured variables of two different measurement circuits to the impedance measured variable of another measurement circuit and monitoring the time profile of the resultant derived variables by comparing one with the other.

The predetermined response may involve a modification of the energy output of the generator. Additionally or alternatively, the predetermined response may also involve outputting a warning signal (for example in the form of a message on a display or in the form of a warning sound).

BRIEF DESCRIPTION OF THE DRAWINGS

The invention is explained below in further detail with reference to the attached drawings, in which.

DETAILED DESCRIPTION OF THE INVENTION

Figure 1:
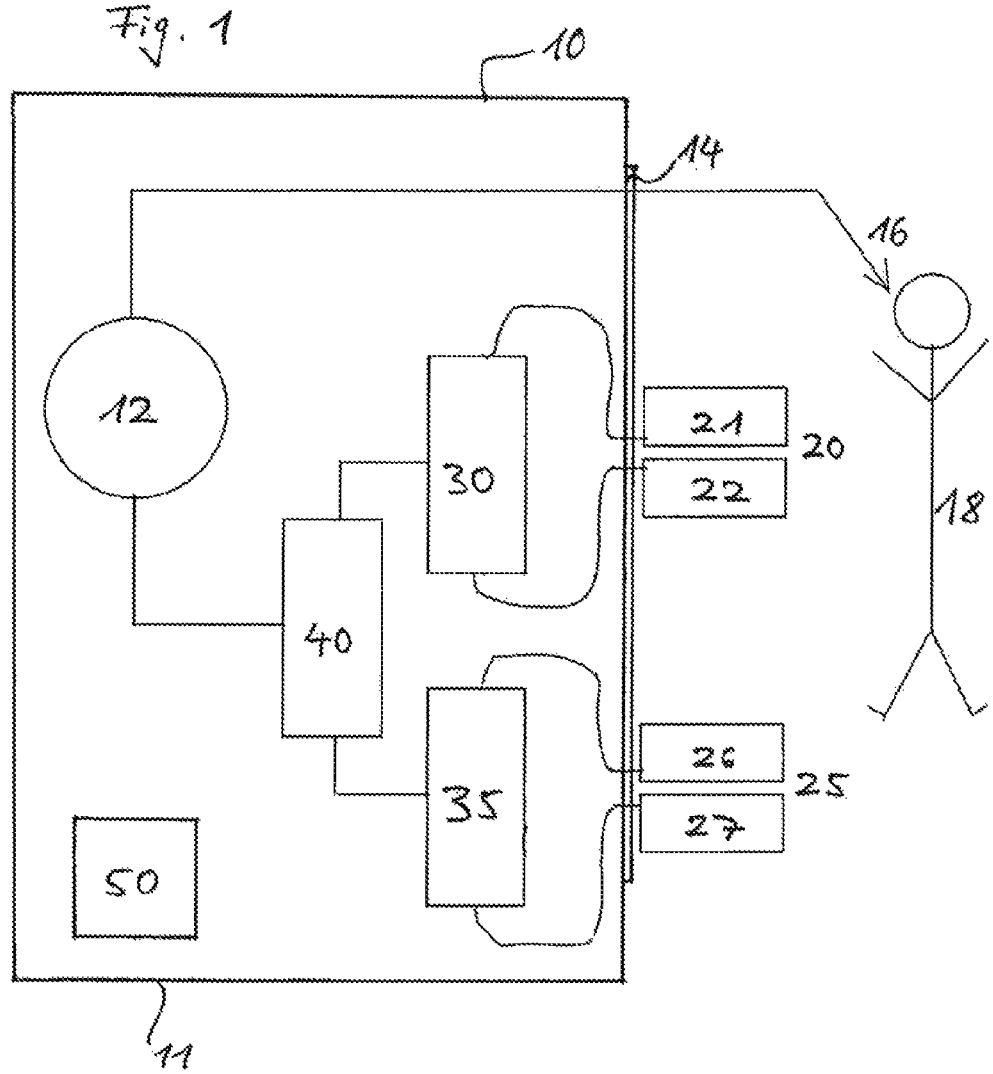
FIG. 1 shows a schematic block diagram of a first exemplary embodiment of a surgical apparatus for the high frequency thermosurgical treatment of body tissue.

Identical or equivalently acting components are designated by identical reference numerals in the figures.

The HF surgical apparatus according to the exemplary embodiment of FIG. 1 is designated 10 overall. It has an apparatus housing 11 which accommodates various electrical and/or electronic components. The components accommodated in the apparatus housing 11 comprise an alternating current generator 12 which provides electrical treatment energy in the form of a high frequency alternating voltage, the frequency of which is for example in the moderate three digit kHz range (for example 300 or 500 kHz). These components furthermore comprise a plurality of (in the present example three) impedance measurement cells 30, 35, 40 where each of the plurality of impedance measurement cells includes first, second and third measurement cells 30, 34, 40 and an electronic evaluation and control circuit 50 connected with the generator 12 and the impedance measurement cells and not shown in greater detail. On the outside of the housing 11 are provided a plurality of connection points, for example constructed as sockets, at which electrode cables may be connected to the surgical apparatus in a manner known per se. The connection points together form an interface connection arrangement designated 14 of the surgical apparatus 10. The electrode cables have on their distal ends one or more electrodes which may be placed on or in the body of a patient 18 to be treated.

Specifically, in the exemplary embodiment shown, the interface connection arrangement 14 permits the connection of at least one application electrode 16 and at least two counter-electrode units 20, 25. The application electrode 16 is positioned in the immediate vicinity of the part of the body to be denatured or otherwise thermally treated. As a rule, it is introduced into the body of the patient 18, for instance in order to position it at the cardiac wall and to sever an excitation pathway (conduction pathway) located there. The counter-electrode units 20, 25 comprise in each case two planar counter-electrodes 21, 22 and 26, 27 respectively, which, for monopolar treatment, are laid externally onto the skin of the patient 18, such that they have the largest possible area of contact with the skin. For example, the counter-electrode units 20, 25 are laid on the patient's back, thigh or chest, an electrically conductive gel often being applied onto the underside of the electrode facing towards the skin in order to improve the contact. In a manner not shown in greater detail, the counter-electrode units 20, 25 in each case comprise a carrier substrate which acts as a common carrier for the two electrodes of the counter-electrode unit in question. Such counter-electrode units with two flat electrodes which are arranged on a common carrier substrate but are not electrically connected are also known in specialist circles as divided counter-electrodes.

Instead of using counter-electrode units with in each case two (or even more) physically contiguous flat electrodes, it is in principle conceivable to use individual electrodes for at least one part of the counter-electrodes 21, 22, 26, 27.

The electrical treatment current output by the generator 12 flows via the application electrode 16 into the body tissue of the patient 18. Current return proceeds via the counter-electrodes 21, 22, 26, 27. Due to the considerably larger area of each of the counter-electrodes 21, 22, 26, 27 in comparison with the application electrode 16, the current density at the counter-electrodes 21, 22, 26, 27 is considerably lower than at the application electrode 16, providing that good, extensive contact of the counter-electrodes 21, 22, 26, 27 with the skin of the patient 18 is maintained. However, as soon as the effective contact area of a counter-electrode with the skin is reduced, for instance because the counter-electrode becomes partially detached from the skin or because severe sweating occurs under part of the counter-electrode, which can bring about a sharp local reduction in conductivity, local spikes in current density may occur at the counter-electrode. Such current density spikes entail a risk of skin charring.

The purpose of the impedance measurement cells 30, 35, 40 is, by impedance measurement, to identify in good time and avoid undesired skin charring at the counter-electrodes.

Each of the impedance measurement cells 30, 35, 40 serves to measure the impedance in an impedance measurement circuit. Due to the plurality of impedance measurement cells 30, 35, 40 present, impedance may accordingly be measured in a plurality of impedance measurement circuits where the plurality of impedance measurement circuits include first, second and third measurement circuits 30, 35, 40. Each of these impedance measurement circuits passes via one or more of the electrodes connectable to the interface connection arrangement 14. The impedance measurement cells 30, 35, 40 supply the impedance measured variables they have detected to the evaluation and control circuit 50, which evaluates the resultant impedance measured variables and controls the energy output of the generator 12 as a function of the measured impedances.

In the specific example of FIG. 1, the impedance measurement cell 30 detects the impedance in a measurement circuit which passes from the measurement cell 30 via the counter-electrode 21 and the patient's body to the counter-electrode 22 and thence back to the measurement cell 30. In this measurement circuit, the two counter-electrodes 21 and 22 are accordingly arranged electrically in series. The part of the patient's body of relevance to impedance in the measurement circuit is substantially restricted to the piece of skin and the underlying tissue between the two counter-electrodes 21, 22. Due to the physically contiguous nature of the two counter-electrodes 21, 22 as a counter-electrode unit ("divided counter-electrode"), there is only a relatively short piece of skin located electrically between the two counter-electrodes 21, 22.

The impedance measurement cell 35, on the other hand, detects impedance in a measurement circuit which passes from the measurement cell 35 via the counter-electrode 26 and the patient's body to the counter-electrode 27 and thence back to the measurement cell 35. In this case too, the two counter-electrodes 21 are arranged electrically in series in the measurement circuit.

In the terminology used in the claims, the two measurement circuits, in which the impedance measurement cells 30, 35 measure impedance, in each case constitute a first measurement circuit. This is because the counter-electrodes of each counter-electrode unit are arranged electrically in series with one another in the circuits.

The impedance measurement cell 40 detects the impedance in a measurement circuit which passes from the measurement cell 40 via the counter-electrode unit 20, thence via the patient's body to the counter-electrode unit 25 and back to the measurement cell 40. In this measurement circuit, the two counter-electrode units 20, 25 are thus arranged electrically in series with one another, the individual counter-electrodes of each of the two counter-electrode units in each case being arranged electrically parallel to one another (i.e. electrodes 21, 22 are arranged parallel to one another, as are electrodes 26, 27). In this case, the part of the patient's body of relevance to measurement circuit impedance is larger than in the cases of the measurement circuits of the measurement cells 30, 35, since the distance between the two counter-electrode units 20, 25 will usually be larger than the distance between the two electrodes of a counter-electrode unit.

In the terminology of the claims, the measurement circuit measured by the measurement cell 40 constitutes a third measurement circuit.

Figure 2:
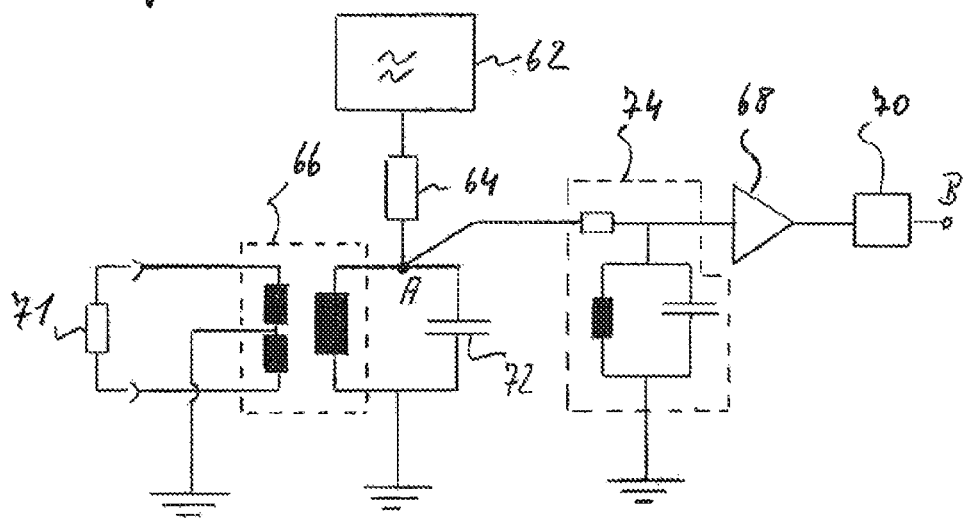
FIG. 2 shows a circuit diagram of an impedance measurement cell of the surgical apparatus of FIG. 1.

The circuit diagram of FIG. 2 shows an example structure of an impedance measurement cell which may be used for impedance measurement between counter-electrodes or between counter-electrode units. The measurement cell operates with an electrical auxiliary signal in the form of an alternating voltage provided by an alternating voltage generator 62, the frequency of which differs from the frequency of the treatment current of the generator 12. Since the auxiliary signal is not intended to have any physiological action on the body, its frequency is for example approx. 100 kHz, but in any event distinctly below the treatment frequency. A resistor 64 is arranged in series with the generator 62, the resistance value of which resistor is large in comparison with the remaining impedances in the impedance measurement circuit, in particular large in comparison with the tissue impedance of the body 18 and with the transition resistances between the skin and counter-electrodes. Together with the resistor 64, the generator 62 forms an alternating current source of constant alternating current amplitude.

The auxiliary alternating current generated by the generator 62 and the resistor 64 is supplied to the primary side of a repeating coil 66. In this manner, an alternating voltage of identical frequency is induced on the secondary side. The secondary side of the repeating coil 66 is electrically connected in a closed circuit with the body 18 of the patient via two or more of the electrodes connected to the surgical apparatus 10, such that a secondary current flows via the electrodes between the secondary side of the repeating coil 66 and the body 18 of the patient. Depending on the tissue or skin impedance prevailing between the electrodes and the contact resistance between the electrodes and the skin (commonly represented by a load resistor 71), the secondary circuit is subjected to a varying load, which is reflected in a correspondingly varying load (attenuation) on the primary side of the repeating coil 66. The voltage amplitude on the primary side at a point A depends on the attenuation of the primary side and consequently on the skin impedance and contact impedance between the skin and applied electrodes. It has been found that this dependency is at least approximately proportional over wide ranges.

The voltage is picked off at point A, amplified by means of an amplifier arrangement 68 and then rectified by means of a rectifier circuit 70. A direct voltage thus prevails at output B of the rectifier circuit 70, the level of which is a measure of the total impedance in the secondary circuit. If the level of this direct voltage changes, this is indicative of a change in tissue impedance brought about, for example, by the onset of charring and/or of a changed contact resistance due to partial detachment of one or more electrodes. The direct voltage at point B, which is an impedance measured variable for the purposes of the invention, is monitored and evaluated by the evaluation and control circuit 50 of the surgical apparatus 10. It may optionally be converted into a digital value for this purpose.

It may furthermore be seen in FIG. 2 that the secondary side of the repeating coil 66 has a central tap, from which the treatment current flows directly or via at least one further repeating coil 66 to earth. The treatment current introduced into the body 18 via the application electrode 16 flows in phase opposition via counter-electrodes connected with the secondary side of the repeating coil 66 into the two secondary coils separated by the central tap. The HF circuit is then completed via the central tap. Due to the phase opposition of the currents flowing in the secondary coils, the related magnetic fields cancel each other out. Therefore, no voltage is induced on the primary side of the repeating coil 66 as a result of the treatment current. The repeating coil 66 behaves "passively" at the treatment frequency. This applies at least for as long as the treatment sub-currents are of identical size in the two secondary coils. If the treatment sub-currents in the secondary coils of the repeating coil 66 are unequal, the difference is transformed to the primary side. This means that, in addition to the auxiliary signal frequency, other frequencies may under certain circumstances also occur on the primary side, such as for example the treatment frequency in the case of asymmetrical treatment sub-currents in the secondary coils. Such other frequencies should, however, have as far as possible no influence on the impedance measured variable at point B, since the intention with the present circuit is to achieve impedance measurement which solely measures the response to the excitation by the auxiliary current.

In order to eliminate unwanted interference from the impedance measured variable at point B, the circuit according to FIG. 2 contains suitable filter means which act as a bandpass for the auxiliary signal frequency while blocking other frequencies which occur under certain circumstances, in particular the treatment frequency. In the example shown, these filter means form two filter stages, the first of which is formed by an LC parallel circuit which is made up of the primary coil of the repeating coil 66 and a capacitor 72 connected in parallel thereto. A further filter stage in the form of an RLC bandpass filter 74 is provided downstream. The two filter stages ensure that substantially only signals having the auxiliary signal frequency of the generator 62 arise at the input of the amplifier arrangement 68.

The various impedance measurement cells 30, 35, 40 of the surgical apparatus 10 of FIG. 1 are all of identical construction. Each contains its own repeating coil 66, its own filter components 72, 74, its own amplifier arrangement 68 and its own rectifier arrangement 70. The auxiliary signal generator 62 (with or without the resistor 64) may be provided jointly for all impedance measurement cells 30, 35, 40.

Figure 3:
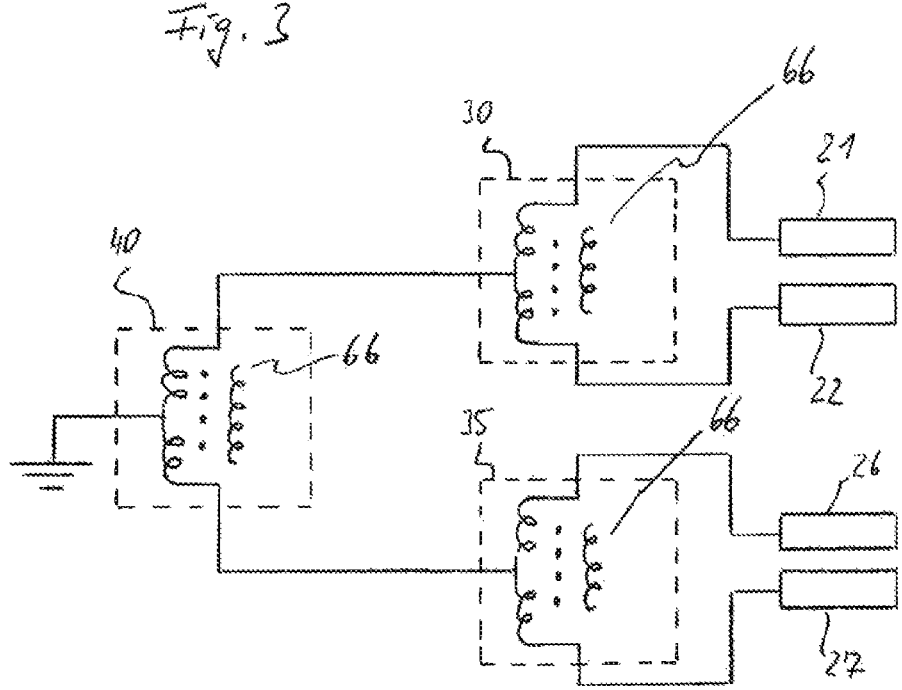
FIG. 3 shows the interconnection of a plurality of impedance measurement cells of the surgical apparatus of FIG. 1.

FIG. 3 shows how the repeating coils 66 present in the measurement cells 30, 35, 40 are interconnected with one another and with the counter-electrodes 21, 22, 26, 27. The impedance measurement cells 30, 35 are directly connected with the counter-electrodes 21, 22 and 26, 27 respectively. To this end, the counter-electrodes in question are each connected with one of the two outer secondary repeater coil terminals of the measurement cell in question. The impedance measurement cell 40, on the other hand, is not directly connected with the counter-electrodes 21, 22, 26, 27. The outer secondary repeater coil terminals of said impedance measurement cell 40 are in each case connected with the central secondary repeater coil terminal (i.e. the central tap) of the measurement cell 30 or the measurement cell 35, while the secondary central tap of the measurement cell 40 is connected to earth and so completes the return path for the treatment current.

In order to provide a numerical example, an auxiliary alternating voltage of approx. 1 V may be applied to the resistor 64. A resistance value of the resistor 64 of approx. 100 kOhm consequently gives rise to a measurement current of approx. 10 µA minus any switching losses. In the attenuated state (with electrodes applied) alternating voltages of the order of magnitude of 1 mV at the frequency of the auxiliary alternating voltage (for example 100 kHz) then typically prevail on the primary side of the repeating coil 66.

In comparison, a treatment current of up to approx. 3 A at a voltage of approx. 200 V can be output via the application electrode 16. Half of this current ideally flows back to earth through each of the two contact surfaces of the substitute resistor 71. Due to the phase opposition of the sub-currents in the two secondary windings of the repeating coil 66, the magnetic fields then cancel each other out. Ideally, therefore, no HF voltage is transferred from the secondary side to the primary side. However, as soon as the currents pass asymmetrically through the two secondary windings, the difference is transformed into the primary winding. An HF voltage of up to approx. 100 V may then be established at point A at the treatment frequency (for example 500 kHz). Relative to this interference voltage, the impedance measurement voltage for determining skin resistance (approx. 1 mA, see above) virtually disappears. The capacitor 72 and in particular the downstream bandpass filter 74 then filter out the "soft" impedance measurement voltage.

Before addressing the evaluation of the measured impedances and the resultant control actions by the evaluation and control circuit 50 in detail, further exemplary configurations of impedance measurement circuits will be presented schematically with reference to FIGS. 4 to 7.

Figure 4:
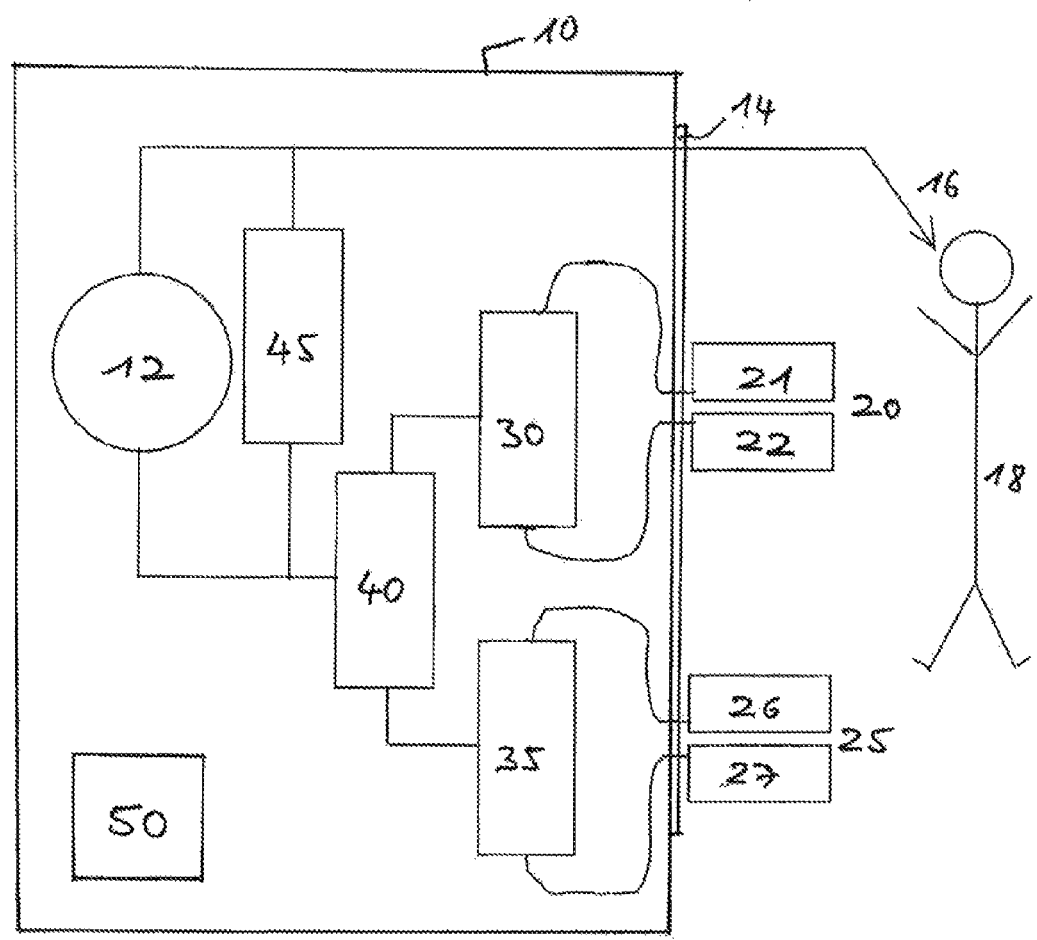
FIG. 4 shows a schematic block diagram of a second exemplary embodiment of an HF surgical apparatus.

The configuration according to FIG. 4 contains in addition to the impedance measurement cells 30, 35, 40 an impedance measurement block 45 which serves to measure impedance in a measurement circuit which passes via the application electrode 16, the body 18 of the patient and all the counter-electrodes 21, 22, 26, 27. It will be noted that in this measurement circuit the counter-electrode units 20, 25 are arranged electrically parallel to one another and in series with the application electrode. In line with the terminology used in the claims, this is a fourth impedance measurement circuit. The impedance measurement block 45 is capable of determining the impedance in its measurement circuit for example from the ratio between voltage amplitude and current amplitude (and optionally from the relative phase angle between voltage and current) of an auxiliary signal introduced into the body via the application electrode 16 together with the treatment current. Corresponding methods for determining impedance are known per se in specialist circles.

Figure 5:
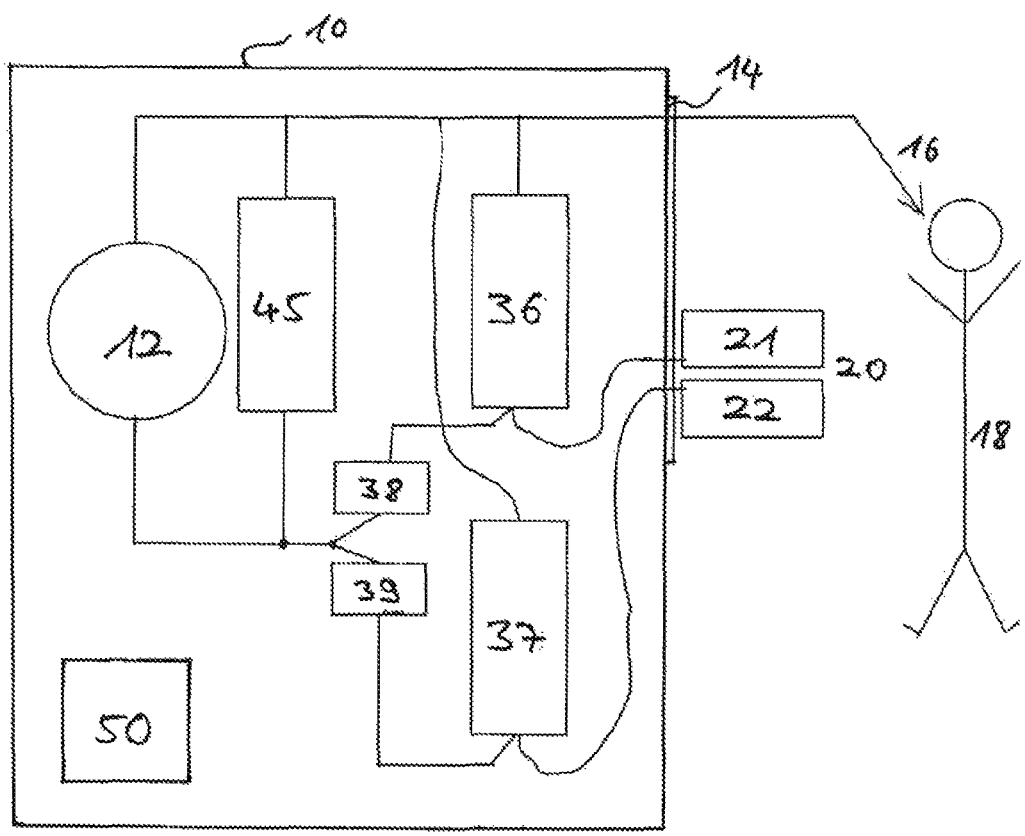
FIG. 5 shows a schematic block diagram of a third exemplary embodiment of an HF surgical apparatus.

The surgical apparatus according to FIG. 5 contains impedance measurement blocks 36, 37 and 45. The impedance measurement block 45 serves, as in FIG. 4, to measure impedance in a measurement circuit passing via the application electrode 16, the patient's body 18 and all the connected counter-electrodes. In the example shown, only the counter-electrode unit 20 is in use; as a result only the two counter-electrodes 21, 22 (namely in series with the application electrode 16 and parallel to one another) are present in the measurement circuit measured by the block 45. The two measurement blocks 36, 37, in contrast, in each case permit impedance measurement in a measurement circuit which passes via the application electrode 16, the body 18 and just one of the two counter-electrodes 21, 22. Specifically, in the example shown, counter-electrode 21 is present in the measurement circuit measured by measurement block 36, while counter-electrode 22 is present in the measurement circuit measured by measurement block 37. In line with the terminology of the claims, the measurement circuits measured by the measurement blocks 36, 37 in each case comprise a second measurement circuit.

In a similar manner to the measurement circuit measured by measurement block 45, these two second measurement circuits are supplied with an auxiliary signal from an auxiliary signal source which is not shown in greater detail.

Here too, the auxiliary signals again have a frequency which differs from the treatment frequency. The auxiliary signal frequencies of the various measurement circuits moreover differ, so that impedance measurements may be made simultaneously in all the measurement circuits.

The following problem must now be solved. The generator 12 supplies current via the application electrode 16 to the patient 18, this treatment current flowing via the counter-electrodes 21, 22 back to the generator 12 or to earth. However, if the two counter-electrodes 21, 22 were simply to be interconnected without further precautions in order to permit return of the treatment current from the two counter-electrodes 21, 22, a short-circuit would arise between the two return lines extending away from the electrodes 21, 22 to the generator 12. In this case, the impedance measurement blocks 36, 37 would provide identical measurement results, since in each case both of the counter-electrodes 21, 22 would be in parallel in the two measurement circuits. A remedy is here provided by means of a filter arrangement consisting of two bandpass filters 38, 39, which filter arrangement allows the treatment frequency and the measurement signal frequency of the impedance measurement device 45 to pass through. The filter arrangement 38, 39 also blocks the measurement signal frequencies of the measurement blocks 36, 37. This ensures that the measurement block 36 measurement signal introduced via the application electrode 16 into the body 18 of the patient flows back to the measurement block 36 not solely via counter-electrode 21 but also via counter-electrode 22. This means that the filter arrangement 38, 39 ensures that measurement block 36 measures the impedance in a measurement circuit containing only counter-electrode 21, but not counter-electrode 22. The filter arrangement 38, 39 likewise prevents the measurement block 37 measurement signal from flowing back via the counter-electrode 21 to the measurement block 37 and so distorting its impedance measurement.

In order to provide an example in numbers, measurement block 36 may use a measurement signal frequency of 100 kHz and measurement block 37 a measurement signal frequency of 105 kHz, while measurement block 45 may for example use a measurement signal frequency of 50 kHz. Filter 38 may here be appropriately designed for measurement block 36 as a 100 kHz band-stop filter and filter 39 for measurement block 37 as a 105 kHz band-stop filter.

Figure 6:
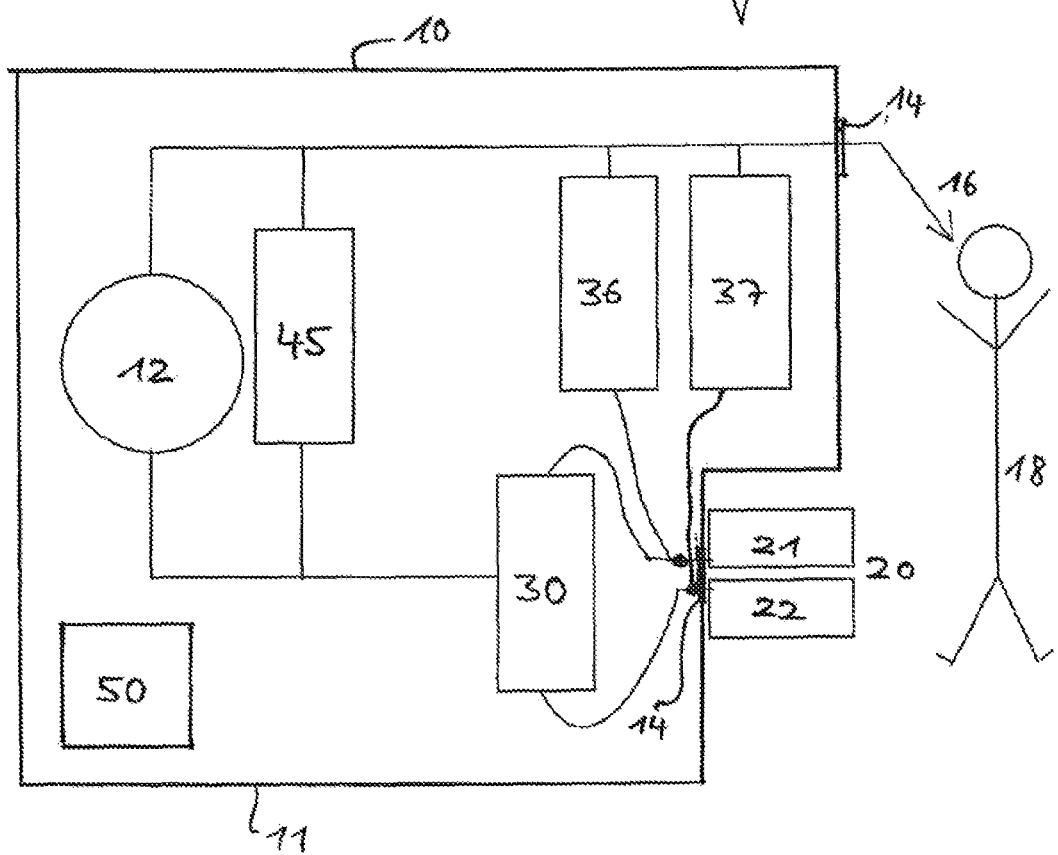
FIG. 6 shows a schematic block diagram of a fourth exemplary embodiment of an HF surgical apparatus.

FIG. 6 shows a variant with an impedance measurement cell 30 and impedance measurement blocks 36, 37 and 45. For clarity's sake, a filter arrangement corresponding to the bandpass filters 38, 39 of FIG. 5 has been omitted from the drawing. Actually, however, a filter arrangement which allows the treatment frequency and the measurement signal frequency of measurement block 45 to pass through is assigned to both of the measurement blocks 36, 37 in FIG. 6, which filter arrangement blocks the measurement signal frequencies of the two measurement blocks 36, 37. For example, suitable bandpass filters may be arranged in the two line branches which connect the counter-electrodes 21, 22 with the outer secondary terminals of the repeating coil 66 present in measurement cell 30 (cf. FIG. 2). The measurement signal frequency of measurement cell 30 conveniently differs from the measurement signal frequencies of the two measurement blocks 36, 37 and from the measurement signal frequency of measurement block 45 and the treatment frequency.

Figure 7:
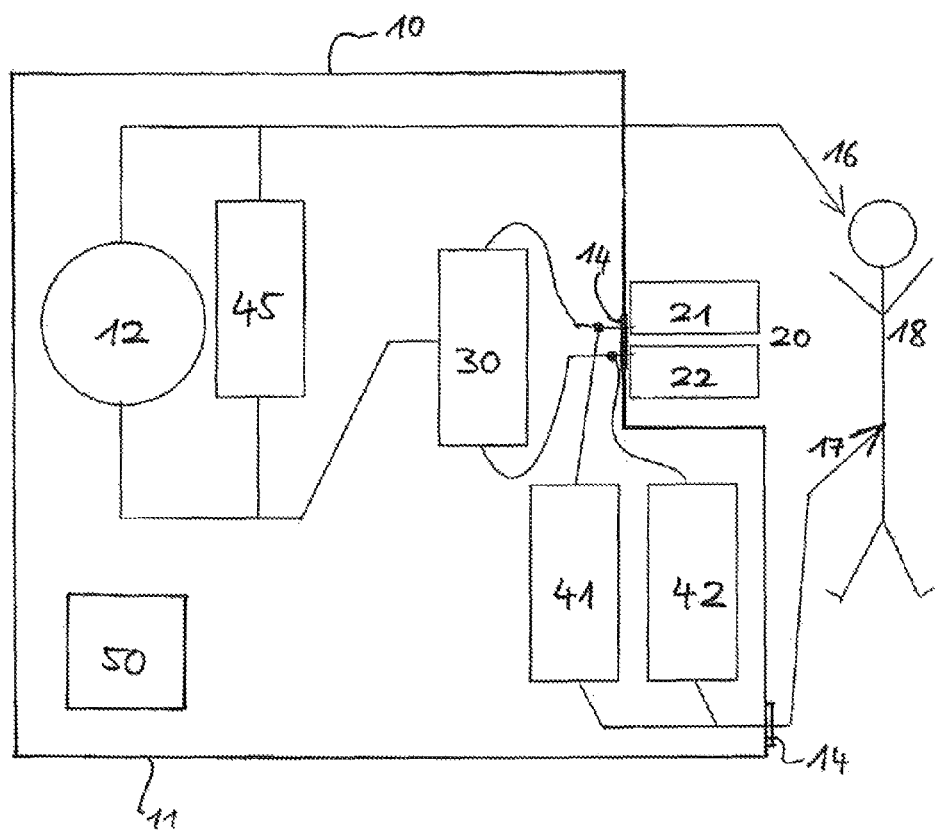
FIG. 7 shows a schematic block diagram of a fifth exemplary embodiment of an HF surgical apparatus.

FIG. 7 finally shows a variant in which two impedance measurement blocks 41, 42 are provided in addition to an impedance measurement cell 30 and an impedance measurement block 45, which in each case permit an impedance measurement in an impedance measurement circuit passing via a needle electrode 17. The needle electrode 17 may likewise be connected to the interface connection arrangement 14 and may be used as a reference electrode which is positioned on the body 18 in a zone between the application electrode 16 and the counter-electrodes 21, 22 (in the example shown, only the counter-electrode unit 20 is again in use) where it picks off a middle potential. Such needle electrodes and the use thereof are known per se in specialist circles. A significant factor in connection with the exemplary embodiment of FIG. 7 is that the needle electrode 17 is used for the impedance measurement. Specifically, an impedance measurement is effected by means of the measurement block 41 in a measurement circuit which passes via the counter-electrode 21, the patient's body 18 and the needle electrode 17. The measurement block 42, in contrast, permits an impedance measurement in a measurement circuit which passes via the counter-electrode 22, the patient's body 18 and the needle electrode 17. The two measurement circuits passing via the needle electrode 17 in each case constitute further examples of a second measurement circuit as defined in the terminology of the claims. In a similar manner to the configurations according to FIGS. 5 and 6, in the configuration of FIG. 7 a filter arrangement (not shown in greater detail) may be assigned to the measurement blocks 41, 42, which filter arrangement blocks the measurement signal frequencies of the measurement blocks 41, 42 and allows the other frequencies which occur (other measurement signal frequencies, treatment frequency) to pass through. In a similar manner to the previous cases, such a filter arrangement ensures that the measurement circuit which is actually measured of the measurement block 41 only passes via the counter-electrode 21 and not also via the counter-electrode 22 and that the measurement circuit which is actually measured of the measurement block 42 only passes via the counter-electrode 22.

In each of the embodiments shown, the evaluation and control circuit 50 thus receives a plurality of impedance measured variables, each representative of the measured impedance in one measurement circuit. The evaluation and control circuit 50 in particular uses the resultant impedance measured variables for controlling the energy output of the generator 12, in order to be able to respond in good time if, as a result of partial detachment of a counter-electrode, there is a risk of skin charring. At least some of the resultant impedance measured variables may be directly monitored by the evaluation and control circuit 50 and used for controlling the surgical apparatus. In addition, the evaluation and control circuit 50 may determine one or more derived variables from one or more of the impedance measured variables and make use of these derived variables in controlling the surgical apparatus. Derived variables may be, for example, a difference between two impedance measured variables and a time derivative of an impedance measured variable.

In particular, the evaluation and control circuit 50 determines from the measured impedance variables a plurality of (two or more) impedance ratios and compares the time profile of the determined impedance ratios. The evaluation and control circuit 50 is preferably to this end capable of relating two impedance measured variables obtained in different impedance measurement circuits in each case to an impedance measured variable obtained in a further impedance measurement circuit and of comparing the resultant ratio variables with one another over their time profile. In this way, it is possible to establish which of the two counter-electrodes of a counter-electrode unit is starting to detach from the skin. Looking at the embodiment of FIG. 6 by way of example, the impedances measured by the two measurement cells 36, 37 may in each case be related to the impedance measured by measurement cell 45. If one of these ratios changes, but the other does not or not to the same extent, this is indicative of a problem with the counter-electrode whose determined impedance ratio is changing. In similar manner, it is conceivable in FIG. 1 to relate the measured impedances of the measurement cells 30, 35 in each case to the measured impedance of measurement cell 40. However, it is of course alternatively or additionally possible to evaluate the measured impedances in each case individually and to use them to control the generator 12.

Evaluation of the resultant impedance measured variables and/or the variables derived therefrom may involve a static limit value check. A static limit value check may consist in comparing at least one of the impedance measured variables and/or at least one of the variables derived therefrom with at least one predetermined threshold value which is set before the beginning of the operation and does not change during the operation. If the variable in question (impedance measured variable or derived variable) reaches the threshold value, the evaluation and control circuit 50 carries out a predetermined response, for example interrupting, reducing or not even enabling energy output from the generator 12. Biological tissue is, however, not a static, reproducible structure. Not all patients are the same. The actual tissue impedance values may thus be dependent on many criteria, for instance on the age of the patient, the water content of the tissue, the positioning of the electrode on the body, fat content, salt content, the blood supply, the nature of the skin, the vicinity to bone, the vicinity to liquid accumulations and vessels etc. The position of the patient and the pressure on the counter-electrodes may also play an important part. The size, material and spacing of the counter-electrodes and the properties of a gel used to improve contact may furthermore also have a major impact on impedance behaviour. Generally applicable static threshold values can therefore be defined only with difficulty, if at all. It has proven sensible to set static threshold values in order not to exceed certain maximum limit values. Certain minimum requirements may be met in this way. Such static control is, however, not regularly adequate.

Measured value evaluation therefore preferably also involves a dynamic limit value check, in which one or more threshold values are set dynamically only during the course of the operation. In particular, such a threshold value is set and optionally adjusted as a function of the measured value of at least one of the impedance measured variables and/or at least one derived variable, should there be any change in the measured value of the impedance measured variable or the derived variable during the operation. This is based on the recognition that the impedance measured in an impedance measurement circuit may be highly dependent on the pressure with which a counter-electrode is pressed against the patient's skin. Pressure changes may then result in significant changes in the measured impedance even without the counter-electrode becoming partially detached from the skin.

In dynamic threshold value setting, an extreme value (minimum or maximum) is determined and stored for an impedance measured variable or a derived variable measured on an ongoing basis (i.e. continuously or at intervals). If the impedance variable or the derived variable falls below (in the case of a minimum) or exceeds (in the case of a maximum) the stored extreme value in the further course of measurement, the stored extreme value is updated. Such extreme value determination may be carried out over the entire duration of the thermosurgical treatment. It is also conceivable to restrict the extreme value determination to a specific part of the duration of treatment, for instance to an initial phase of treatment. Depending on the stored extreme value, at least one threshold value is now set, for example by raising or lowering the stored extreme value by a predetermined percentage or absolute proportion which, if desired, is predeterminable by the user. In this way an individually suitable threshold value may be set for the particular patient and the particular apparatus system used. A change to the stored extreme value is then accompanied by a change to the threshold value determined on the basis thereof. If the threshold value dynamically set in this manner is reached in the course of the operation, the evaluation and control circuit 50 carries out a predetermined response in a similar manner as with the static limit value check. This may in particular involve a change to the energy output of the generator 12. It is alternatively or additionally conceivable that, when a dynamically set threshold value and/or a statically set threshold value is reached, a warning signal (optical, acoustic) is output which notifies the user of the critical contact resistance of the counter-electrodes.

The above dynamic limit value check principle will be illustrated with a numerical example. The impedance measurement via the series connection of the counter-electrodes 21, 22 by means of the measurement cell 30 in FIG. 1 will be taken into account here (the same applies to the impedance measurement via the series connection of the counter-electrodes 26, 27 by means of the measurement cell 35). As soon as the counter-electrode unit 20 with the two counter-electrodes 21, 22 is placed on the body 18 of the patient, from the standpoint of the surgical apparatus 10 there occurs a change in impedance from infinite (no contact of the counter-electrode unit 20 with the patient) to a finite, lower impedance value. When the counter-electrode unit 20 is initially gently fixed onto the skin by the theatre nurse, an impedance value of $55\Omega$ may for example be found between the two counter-electrodes 21, 22. The evaluation and control circuit 50 stores the value of $55\Omega$ as an instantaneous minimum. After the initial gentle fastening, the theatre nurse will press the counter-electrode unit 20 more firmly onto the skin and for example strap it down tightly. The measured impedance then declines, for example to a value of for instance $42\Omega$. The control and evaluation circuit 50 now stores this lower value as the instantaneous minimum. If the patient is not lying on the counter-electrode unit 20 during treatment, the value will not generally drop any further below the stored value of $42\Omega$ over the remaining course of the operation. If, on the other hand, the patient is turned for the operation in such a way that he/she is lying on the counter-electrode unit 20 and so pressing his/her body weight against the counter-electrode unit 20, it may be that the value will again fall below the previously stored minimum value. In this case, the stored minimum value is updated once more. Otherwise, it may be assumed that the minimum will remain at the stored value of $42\Omega$ for the remainder of the treatment.

On the basis of the stored minimum, the evaluation and control circuit 50 sets one or more upper limit values which may not be exceeded at least during specific phases of the treatment procedure. For example, a first dynamic threshold value may be set 15% above the stored minimum value and a second dynamic limit value 20% above the stored minimum value. Since patient movement during HF output should not immediately give rise to an error message, the higher limit value may be applied during HF output as a compromise between safety and the treatment objective. The lower limit value, which only allows a tolerance of 15%, may for example be used as an enabling threshold before the HF energy is switched on. It has been found that, when upper thresholds are set by adding approx. 10% to approx. 20% to the stored impedance minimum, the frequency of false or trivial alarms can in practice be distinctly reduced.

A value of 80Ω may, for example, be set as a static limit value for the impedance between the counter-electrodes 21, 22, a value which is distinctly above the thresholds which may be anticipated for the dynamic limit value check. The prerequisite for HF output even to proceed is that the measured impedance minimum and optionally also the dynamic limit values calculated therefrom are below the static limit value. In this respect, the evaluation and control circuit 50 carries out a combination of static and dynamic limit value checking.

The invention claimed is:

1. An apparatus for thermosurgery comprising:
   a generator for supplying high frequency electrical treatment energy;
   first and second counter-electrode units each including a pair of planar counter-electrodes adapted to be placed on a body of a patient;
   an interface connection system configured to allow connecting thereto an application electrode to be positioned in an area of a treatment site on or in the body of the patient, and the first and second counter-electrode units; and
   impedance measurement circuitry defining a plurality of measurement circuits and including a plurality of measurement cells to measure impedance in the plurality of measurement circuits, wherein the plurality of measurement circuits includes first, second and third measurement circuits and the plurality of measurement cells includes first, second and third measurement cells, wherein the first measurement cell is configured to measure impedance in the first measurement circuit, the second measurement cell is configured to measure impedance in the second measurement circuit, and the third measurement cell is configured to measure impedance in the third measurement circuit,
   wherein the first measurement circuit leads through the pair of planar counter-electrodes of the first counter-electrode unit, which are arranged electrically in series in the first measurement circuit,
   wherein the second measurement circuit leads through the pair of planar counter-electrodes of the second counter-electrode unit, which are arranged electrically in series in the second measurement circuit, and
   wherein the third measurement circuit leads through the first and second counter-electrode units, which are arranged electrically in series in the third measurement circuit, wherein the pair of planar counter-electrodes of the first counter-electrode unit are arranged electrically parallel to one another in the third measurement circuit and the pair of planar counter-electrodes of the second counter-electrode unit are arranged electrically parallel to one another in the third measurement circuit.

2. The apparatus of claim 1, wherein the plurality of measurement circuits includes a fourth measurement circuit and the plurality of measurement cells includes a fourth measurement cell configured to measure impedance in the fourth measurement circuit, wherein the fourth measurement circuit leads through the application electrode and at least two planar counter-electrodes from the pair of planar counter-electrodes of the first counter-electrode unit and the pair of planar counter-electrodes of the second counter-electrode unit, wherein the at least two planar counter-electrodes are arranged electrically parallel to one another in the fourth measurement circuit.

3. The apparatus of claim 1, further comprising an evaluation and control device configured to:
   monitor at least one impedance measured variable representative of the impedance in at least one of the plurality of measurement circuits; and
   bring about a predetermined response depending on whether a monitored impedance measured variable fulfils a predefined condition.

4. The apparatus of claim 3, wherein the evaluation and control device is configured to bring about the predetermined response depending on whether the monitored impedance measured variable reaches a threshold value set as a function of at least one previous value of the monitored impedance measured variable.

5. The apparatus of claim 4, wherein the evaluation and control device is configured to set the threshold value as a function of a measured extreme value of the monitored impedance measured variable.

6. The apparatus of claim 1, further comprising an evaluation and control device configured to:
   monitor at least one variable derived from at least one impedance measured variable representative of the impedance in at least one of the plurality of measurement circuits; and
   bring about a predetermined response depending on whether a derived variable fulfils a predefined condition.

7. The apparatus of claim 6, wherein the evaluation and control device is configured to bring about the predetermined response depending on whether the derived variable reaches a threshold value set as a function of at least one previous value of the derived variable.

8. The apparatus of claim 7, wherein the evaluation and control device is configured to set the threshold value as a function of a measured extreme value of the derived variable.

9. The apparatus of claim 6, wherein the evaluation and control device is configured to determine, as a derived variable, a ratio of impedance measured variables of two of the plurality of measurement circuits.

10. The apparatus of claim 9, wherein the evaluation and control device is configured to relate an impedance measured variable of each of the two measurement circuits to an impedance measured variable of another of the plurality of measurement circuits and to monitor a time profile of resultant derived variables.

* * * * *